(12) United States Patent
Tsai

(10) Patent No.: US 7,141,039 B2
(45) Date of Patent: Nov. 28, 2006

(54) STRUCTURE OF SAFETY HYPODERMIC SYRINGE

(76) Inventor: Jin-Chou Tsai, 18/F, No. 95, Roosevelt Rd., Sec. 2, Taipei City (TW)

( * ) Notice: Subject to any disclaimer, the term of this patent is extended or adjusted under 35 U.S.C. 154(b) by 119 days.

(21) Appl. No.: 10/958,419

(22) Filed: Oct. 6, 2004

(65) Prior Publication Data

US 2006/0074385 A1    Apr. 6, 2006

(51) Int. Cl.
*A61M 5/00* (2006.01)
*A61M 5/32* (2006.01)

(52) U.S. Cl. ...................... 604/110; 604/195
(58) Field of Classification Search ............... 604/110, 604/187, 194, 198, 200, 217–218, 221, 226, 604/228, 240, 241; 128/919
See application file for complete search history.

(56) References Cited

U.S. PATENT DOCUMENTS 5,401,246 A * 3/1995 Mazur et al. ............... 604/110
2003/0212367 A1* 11/2003 Shue et al. ................. 604/196

* cited by examiner

*Primary Examiner*—LoAn H. Thanh
(74) *Attorney, Agent, or Firm*—Rosenberg, Klein & Lee

(57) ABSTRACT

A safety hypodermic syringe in which the plunger is breakable into a front part and a rear part after the service of the safety hypodermic syringe so that the front part can be kept with the needle assembly inside the barrel and the rear part can be inserted into the front side of the barrel and capped on the needle cannula of the needle assembly inside the barrel to prevent contamination.

3 Claims, 3 Drawing Sheets

STRUCTURE OF SAFETY HYPODERMIC SYRINGE

BACKGROUND OF THE INVENTION

1. Field of the Invention

The present invention relates to a hypodermic syringe and more particularly, to a safety hypodermic syringe, which prevents contamination after its service and, which is inexpensive to manufacture.

2. Description of the Related Art

U.S. Pat. No. 6,423,033 B1, issued to the present inventor, discloses a safety hypodermic syringe in which a pull handle is inserted into the plunger and adapted to pull the needle assembly backwards to the inside of the plunger in the barrel after the service of the safety hypodermic syringe. The pull handle has a middle neck through which the rear part of the pull handle can easily be separated from the front part of the pull handle by bending, enabling the separated rear part of the pull handle to be inserted into the plunger in the barrel and hooked up with the front part of the pull handle.

The aforesaid safety hypodermic syringe is functional, however the arrangement of the plunger and the pull handle complicates the structure, resulting in a high manufacturing cost.

SUMMARY OF THE INVENTION

The present invention has been accomplished under the circumstances in view. It is the main object of the present invention to provide a safety hypodermic syringe, which keeps the needle assembly received inside the barrel after the service of the safety hypodermic syringe to prevent contamination. It is another object of the present invention to provide a safety hypodermic syringe, which is inexpensive to manufacture. According to one aspect of the present invention, the safety hypodermic syringe is comprised of a barrel, a needle holder, a needle assembly, and a plunger, wherein the plunger is breakable into a front part and a hollow rear part after the service of the safety hypodermic syringe so that the front part can be kept with the needle assembly inside the barrel and the hollow rear part can be inserted into the front side of the barrel and capped on the needle cannula of the needle assembly inside the barrel to prevent contamination. According to another aspect of the present invention, the needle holder has a male retainer at the rear side, and the plunger has a female retainer at the front side for coupling to the male retainer to secure the needle holder to the plunger. According to still another aspect of the present invention, the barrel has an inside annular flange extended around the inside wall near the front side, and the plunger has locating notches extended around the periphery of the hollow rear part thereof for engagement with the inside annular flange of the barrel upon insertion of the hollow rear part of the plunger into the front side of the barrel after the service of the safety hypodermic syringe.

DETAILED DESCRIPTION OF THE PREFERRED EMBODIMENT

Figure 1:
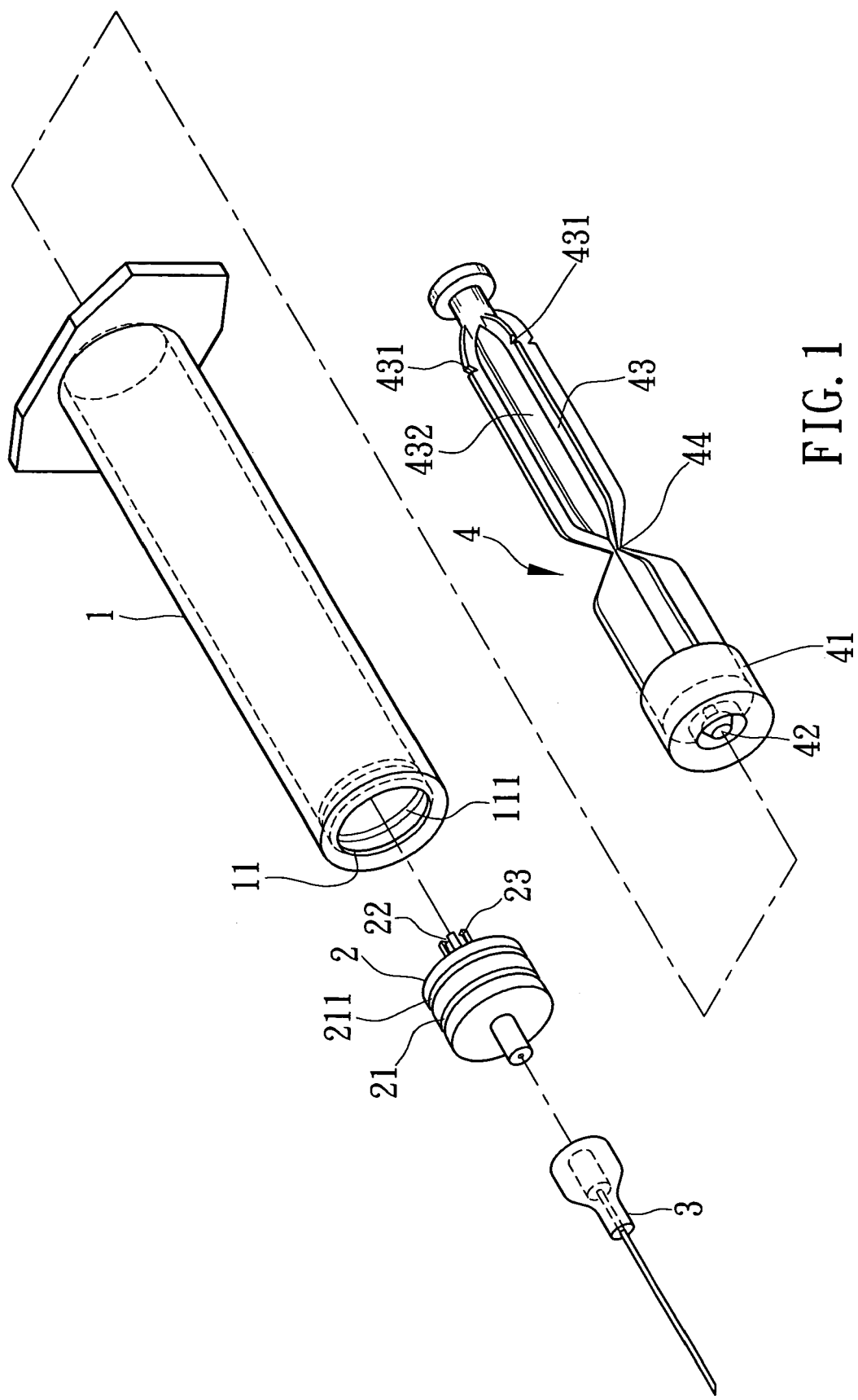
FIG. 1 is an exploded view of a safety hypodermic syringe according to the present invention.
Figure 2:
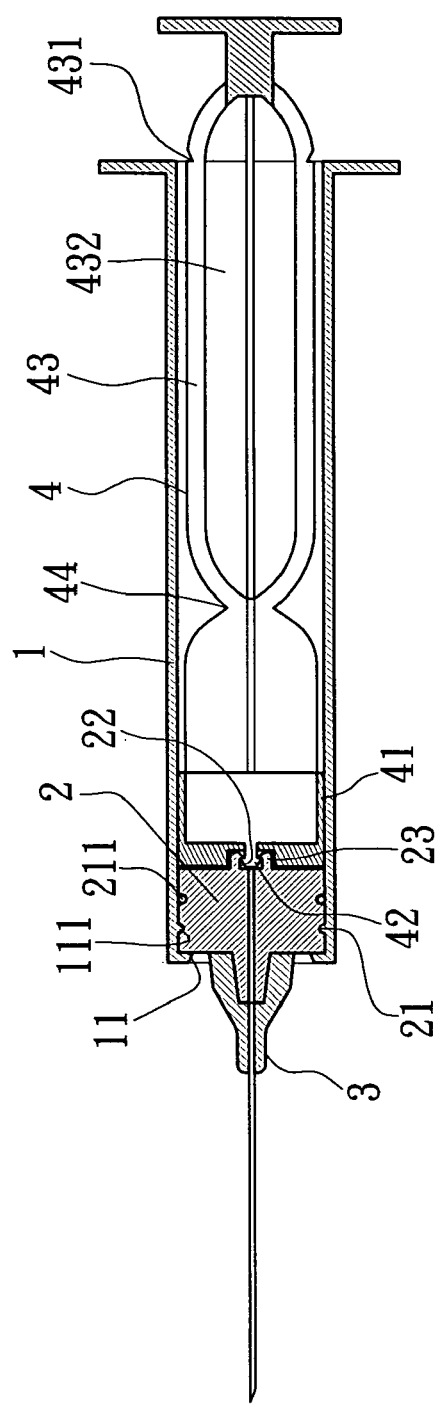
FIG. 2 is a sectional assembly view of the safety hypodermic syringe according to the present invention.
Figure 3:
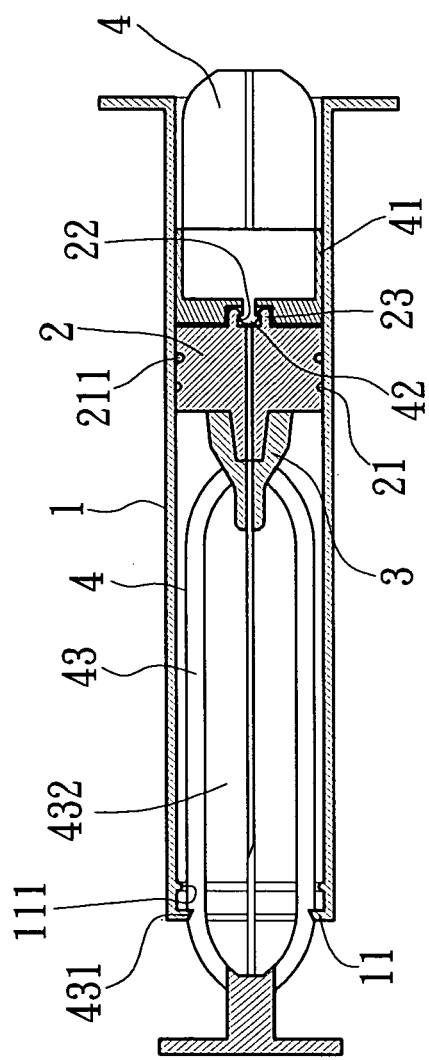
FIG. 3 shows the needle assembly received inside the barrel after the service of the safety hypodermic syringe according to the present invention.

Referring to FIGS. 1~3, a safety hypodermic syringe in accordance with the present invention is shown comprised of a barrel 1, a needle holder 2, a needle assembly 3, and a plunger 4. The barrel 1 has an inside annular flange 111 extended around the inside wall near the front end 11. The needle holder 2 is a cylindrical member mounted in the front side of the barrel 1, having a seal ring 211 mounted around the periphery thereof and kept in close contact with the inside wall of the barrel 1, an outside annular groove 21 extended around the periphery and coupled to the inside annular flange 111 of the barrel 1, and a tubular split coupling member 22 axially backwardly extended from the center of the rear side thereof and defining therein a coupling hole 23. The needle assembly 3 is fastened to the front side of the needle holder 2 and suspending outside the barrel 1. The plunger 4 is axially slidably inserted into the barrel 1 from the rear side, having a cylindrical front stopper head 41 disposed in close contact with the inside wall of the barrel 1, a front arrowhead retainer 42 disposed at the center of the front side of the front stopper head 41 and engageable into the coupling hole 23 of the needle holder 2 to secure the needle holder 2 to the plunger 4, a longitudinally ribbed hollow plunger body 43, a breakable neck 44 connected between the cylindrical front stopper head 41 and the longitudinally ribbed hollow plunger body 43, an elongated needle receiving chamber 432 defined in the longitudinally ribbed hollow plunger body 43 and axially extended to the breakable neck 44, and a plurality of locating notches 431 respectively formed in the ribs of the longitudinally ribbed hollow plunger body 43.

When pushed to the plunger 4 forwards to squeeze fluid medicine out of the barrel 1 through the axially extended center through hole (not shown) of the needle holder 2 and the needle assembly 3, the front arrowhead retainer 42 of the plunger 4 will be forced into engagement with the coupling hole 23 of the needle holder 2 to secure the needle holder 2 to the plunger 4. After the service of the safety hypodermic syringe, the plunger 4 is pulled backwards to carry the needle holder 2 and the needle assembly 3 backward to the inside of the barrel 1, and then a biasing force is applied to the rear part of the plunger 4 to break the breakable neck 44, and then the broken rear part, i.e., the longitudinally ribbed hollow plunger body 43 is inserted into the barrel 1 from the front side to force the locating notches 431 into engagement with the inside annular flange 111 of the barrel 1 and to have the needle cannula of the needle assembly 3 be received in the elongated needle receiving chamber 432 in the longitudinally ribbed hollow plunger body 43 inside the barrel 1.

Figure 4:
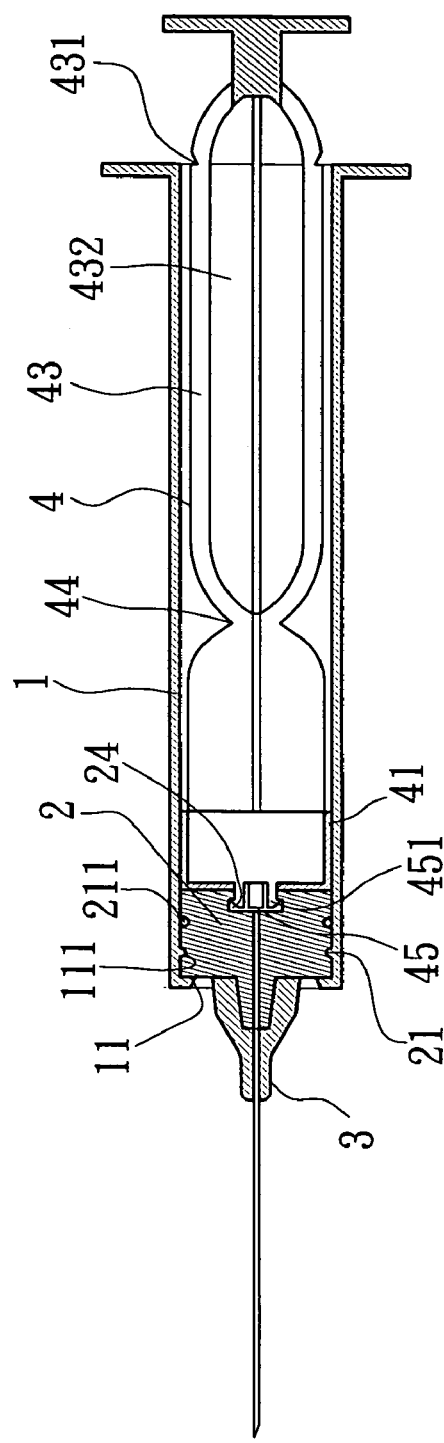
FIG. 4 is a sectional view of an alternate form of the safety hypodermic syringe according to the present invention.
Figure 5:
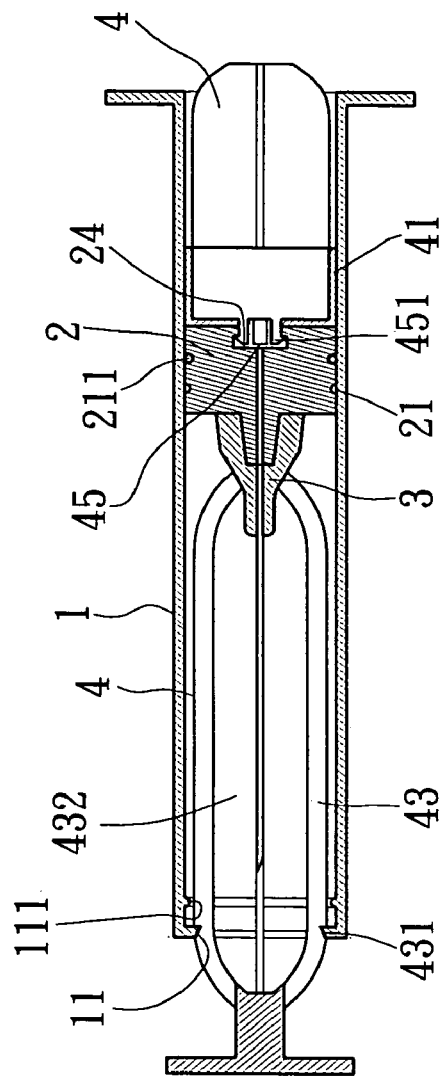
FIG. 5 shows the needle assembly of the safety hypodermic syringe of FIG. 4 received inside the barrel after the service of the safety hypodermic syringe.

FIGS. 4 and 5 show an alternate form of the present invention. This embodiment is substantially similar to the aforesaid embodiment shown in FIGS. 1~3 with the exception that the plunger 4 has a male retainer 45 formed of spring hooks 451 and forwardly extended from the center of the front side of the front stopper head 41, and the needle holder 2 has a female retainer, i.e., a retaining hole 24 formed in the rear side for receiving the male retainer 45 of the plunger 4.

A prototype of safety hypodermic syringe has been constructed with the features of FIGS. 1~5. The safety hypodermic syringe functions smoothly to provide all the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A safety hypodermic syringe comprising a barrel, said barrel having a front side and a rear side, a needle holder fastened to the front side of said barrel, a needle assembly fastened to said needle holder and suspending outside said barrel, and a plunger inserted through the rear side of said barrel into the inside of said barrel and axially movable forwards/backwards to produce a vacuum force in said barrel or squeeze a fluid out of said barrel through said needle stopper and said needle assembly, wherein:

said barrel has an inside annular flange extended around the inner diameter near the front side thereof;

said needle holder has a seal ring mounted around the periphery thereof and kept in close contact with the peripheral wall of said barrel, an outside annular groove extended around the periphery and coupled to the inside annular flange of said barrel, and a female retainer disposed at a rear side thereof;

said plunger has a cylindrical front stopper head disposed in close contact with the peripheral wall of said barrel, a male retainer disposed at a front side of said front stopper head and adapted to engage said female retainer for enabling said needle holder and said needle assembly to be pulled backwards with said plunger and received to the inside of said barrel upon a backward movement of said plunger relative to said barrel after the service of the safety hypodermic syringe, a longitudinally ribbed hollow plunger body, a breakable neck connected between said cylindrical front stopper head and said longitudinally ribbed hollow plunger body through which said plunger is breakable by bending, and an elongated needle receiving chamber defined in said longitudinally ribbed hollow plunger body and axially extended to said breakable neck for capping on said needle assembly when the user breaks said breakable neck and inserts the broken longitudinally ribbed hollow plunger body into the front side of said barrel after the service of the safety hypodermic syringe, said plunger further has a plurality of locating notches formed in ribs of said longitudinally ribbed hollow plunger body for engagement with said inside annular flange of said barrel upon insertion of the broken longitudinally ribbed hollow plunger body into the front side of said barrel after the service of the safety hypodermic syringe.

2. The safety hypodermic syringe as claimed in claim 1, wherein said male retainer of said plunger is an arrowhead retainer; said female retainer is a tubular split coupling member axially backwardly extended from the rear side of said needle holder and defining therein a coupling hole for receiving said arrow head retainer.

3. The safety hypodermic syringe as claimed in claim 1, wherein said male retainer of said plunger is formed of spring hooks and forwardly extended from said front stopper head; said female retainer is a retaining hole formed in the rear side of said needle holder for receiving said spring hooks.

\* \* \* \* \*